US005443070A

United States Patent [19]

Mniece

[11] Patent Number: 5,443,070

[45] Date of Patent: Aug. 22, 1995

[54] ULTRASOUND PRODE WITH BANKS OF INTERCONNECTED ELECTROSTRICTIVE TRANSDUCER ELEMENTS

[75] Inventor: James R. Mniece, Waltham, Mass.

[73] Assignee: Hewlett-Packard Company, Palo Alto, Calif.

[21] Appl. No.: 291,637

[22] Filed: Aug. 17, 1994

[51] Int. Cl.⁶ .......... A61B 8/00

[52] U.S. Cl. .......... 128/661.01; 73/626

[58] Field of Search .......... 128/660.08, 660.03, 128/660.05, 661.01, 662.03; 73/625, 626, 627, 628; 310/313 A

[56] References Cited

U.S. PATENT DOCUMENTS 4,141,347 2/1979 Green et al. .......... 128/660.05
4,633,308 12/1986 Dukes et al. .......... 128/661.01
5,031,626 7/1991 Hassler et al. .......... 128/660.03

*Primary Examiner*—George Manuel
*Attorney, Agent, or Firm*—Edward L. Miller

[57] ABSTRACT

A probe in an ultrasound imaging system uses electrostrictive transducer elements that exhibit little or no piezoelectric properties when in an unbiased state, but do exhibit them when a bias is applied. A linear array of a large number of electrostrictive transducer elements in a probe are provided with an aperture that is shifted across the probe by biasing on and off banks of interconnected electrostrictive transducer elements. The progression of transducer elements from one end of the probe to the other is divided or grouped into adjacent banks of consecutive transducer elements. Each bank has the same number (n) of transducer elements. Each of the n-many transducer elements within a bank has a bias terminal, a signal return or ground terminal and a driven terminal. All the ground terminals are common and connected to a signal return, or ground. The driven terminal of each transducer element in a bank is connected in parallel with the corresponding transducer element in every other bank. Within each bank all bias terminals are connected in parallel, but each bank has a separate bias. At any given time only one bank is biased on. Thus, each of the transducer elements within the banks is excited in a cyclic fashion while advancing the selected bank once every cycle.

2 Claims, 4 Drawing Sheets

ULTRASOUND PRODE WITH BANKS OF INTERCONNECTED ELECTROSTRICTIVE TRANSDUCER ELEMENTS

BACKGROUND OF THE INVENTION

Ultrasound imaging is a noninvasive way of investigating with sound waves structures concealed within a body. The generation of the incident sound waves and the reception of their reflections are accomplished with ultrasound transducers, which are usually of piezoelectric material. The transducers produce a burst of ultrasound when excited by a suitable pulse of voltage (say, in the 50–200 volt range for imaging, and in the 5–50 volt range for doppler). It often happens that, owing to the nature of the imaging application, the probe contains a moderate to large number of transducers. In some such applications the number of transducer elements is in the hundreds, the better to achieve a range of spatial perspectives for the object or structure being viewed. In such a case only a subset of the total number of transducer elements is in use at any one time; that subset defines an aperture whose location is moved along the probe in a regular fashion during the imaging process. The conventional way to define the location of the aperture is with a bank of high voltage switches. The high voltage switches connect the transducer elements that are to be the aperture to a collection of transmit and receive circuits in a unit called a scanner. Thus, the notion of a moving aperture for a probe having several hundred transducer elements requires an extensive high voltage switching arrangement, in conjunction with a scanner. The switching arrangement is complex, bulky and expensive; it would be desirable if a simpler way of switching were possible so that the size, complexity and cost of the switching arrangement could be reduced.

SUMMARY OF THE INVENTION

A reduction in the complexity and cost of a moving aperture probe for an ultrasound imaging system may be obtained by using electrostrictive transducer elements. An electrostrictive material is one which exhibits little or no piezoelectric properties when in an unbiased state, but does exhibit them when a bias is applied. A linear array of a large number of transducer elements in a probe may be provided with an aperture that can be shifted across the probe by using electrostrictive transducer elements. The progression of transducer elements from one end of the probe to the other is divided or grouped into adjacent banks of consecutive transducer elements. Each bank has the same number, say n, of transducer elements. Each of the n-many transducer elements within a bank has a bias terminal and a driven terminal. The driven terminal of each transducer dement in a bank is connected in parallel with the corresponding transducer element in certain other banks. All of the bias terminals within a bank are common and each such point is connected to a suitable bias voltage, which is also a good AC ground so that it may function as a signal return path for the excitation of the transducer elements. Likewise, the circuitry in the scanner provides a suitable return path for the application of bias. At any given time only those adjacent banks containing the current location of the aperture are biased on. Thus, it is possible to excite only the transducer elements within the aperture while periodically advancing the aperture across the probe in steps of one transducer element.

DESCRIPTION OF A PREFERRED EMBODIMENT

This disclosure discusses a use for electrostrictive material. The composition and properties of this class of materials is described in the appropriate literature. See, for example, the article entitled "Electrostrictive Materials for Ultrasonic Probes in the $Pb(Mg_{\frac{1}{3}}Nb_{\frac{2}{3}})O_3$-$PbTiO_3$ System" which appear in Japanese Journal of Applied Physics, Vol. 28(1989) Supplement 28-2, pp. 101–104.

Figure 1:
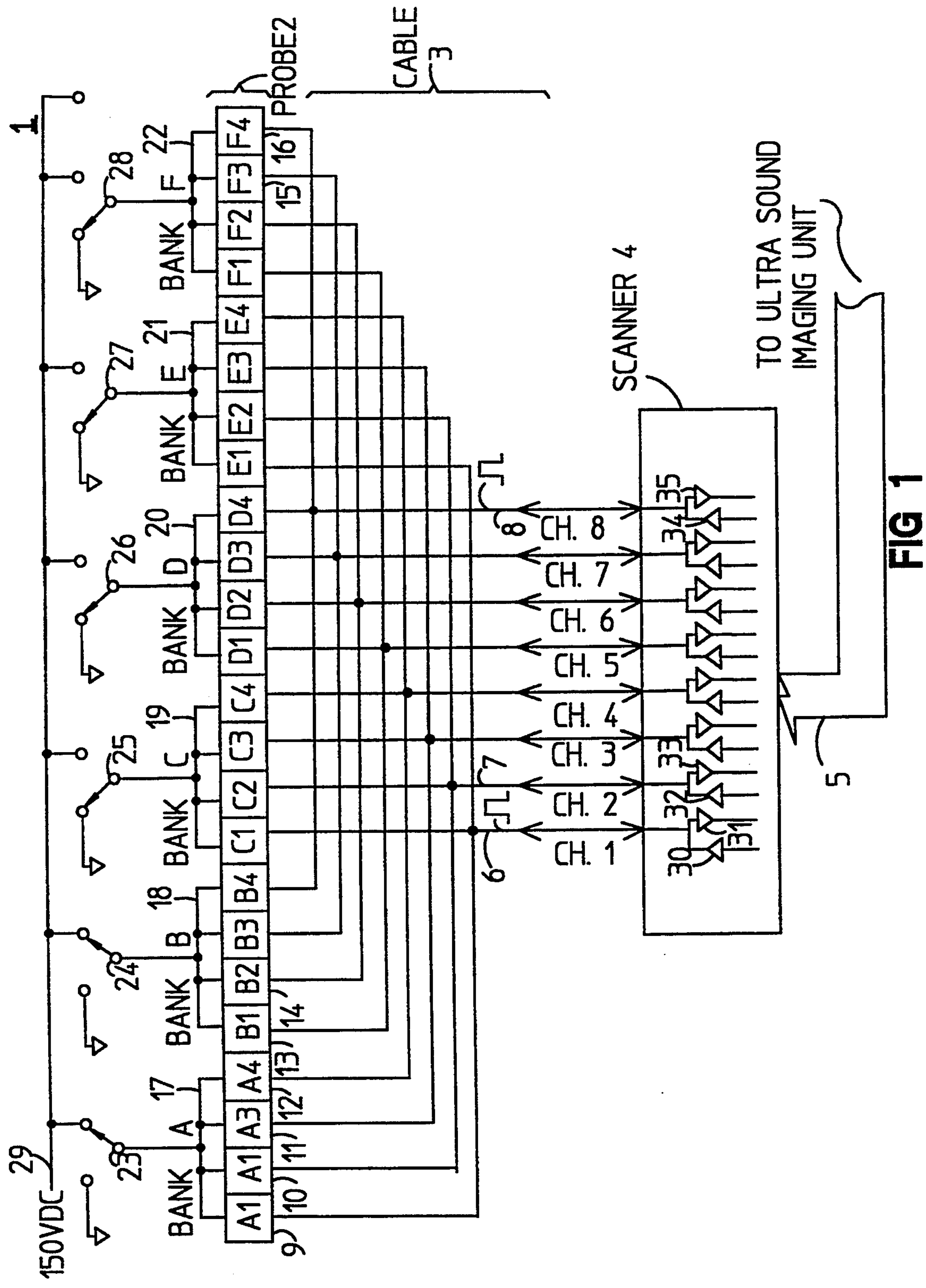
FIG. 1 is a simplified block diagram of an ultrasound probe with banks of interconnected electrostrictive transducer elements, and showing banks selected for positioning an aperture at an extreme location on one side of the probe.
Figure 2:
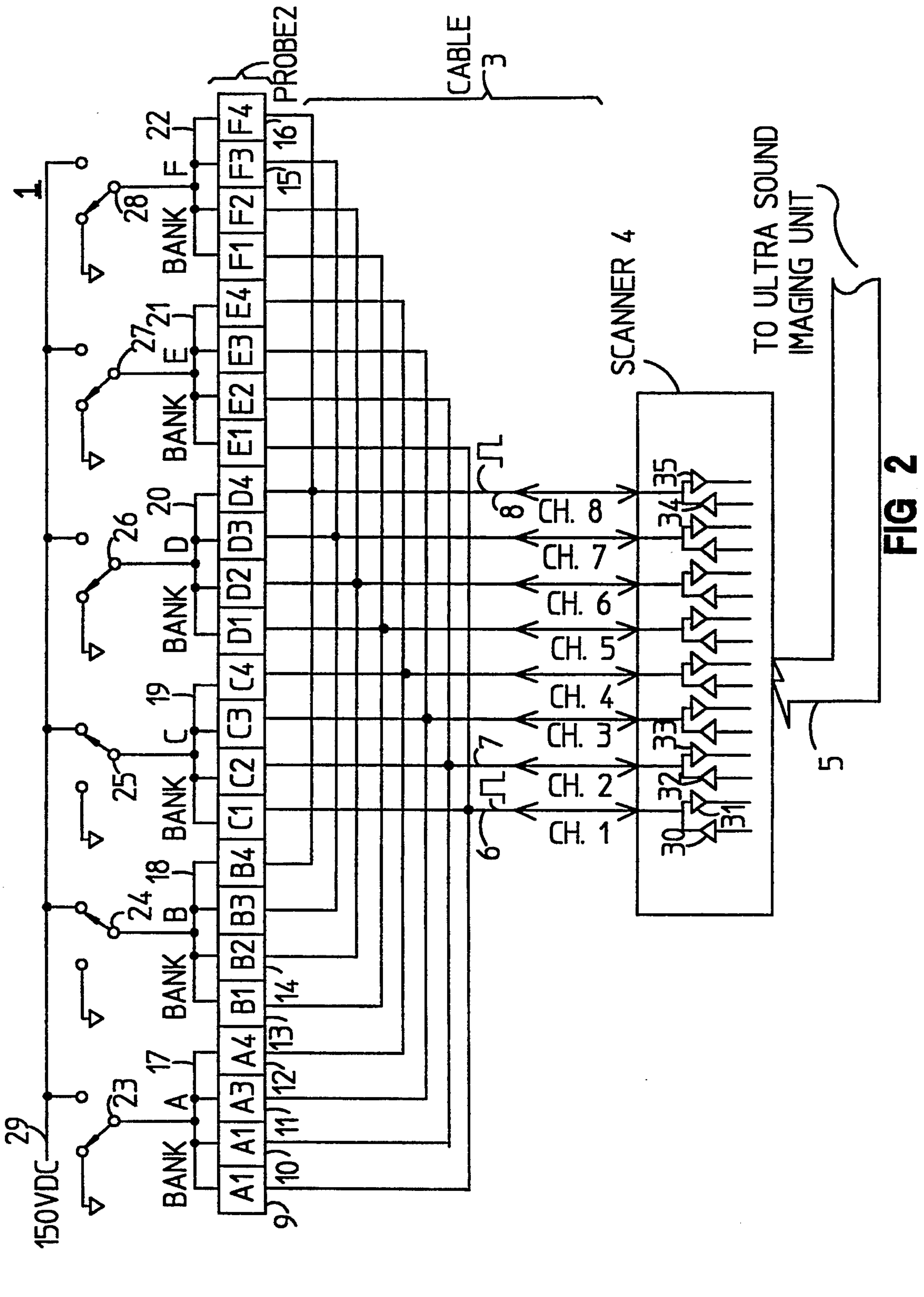
FIG. 2 is the same block diagram as in FIG. 1, but showing a sequentially next selection of banks for a nearby position of the aperture.
Figure 3:
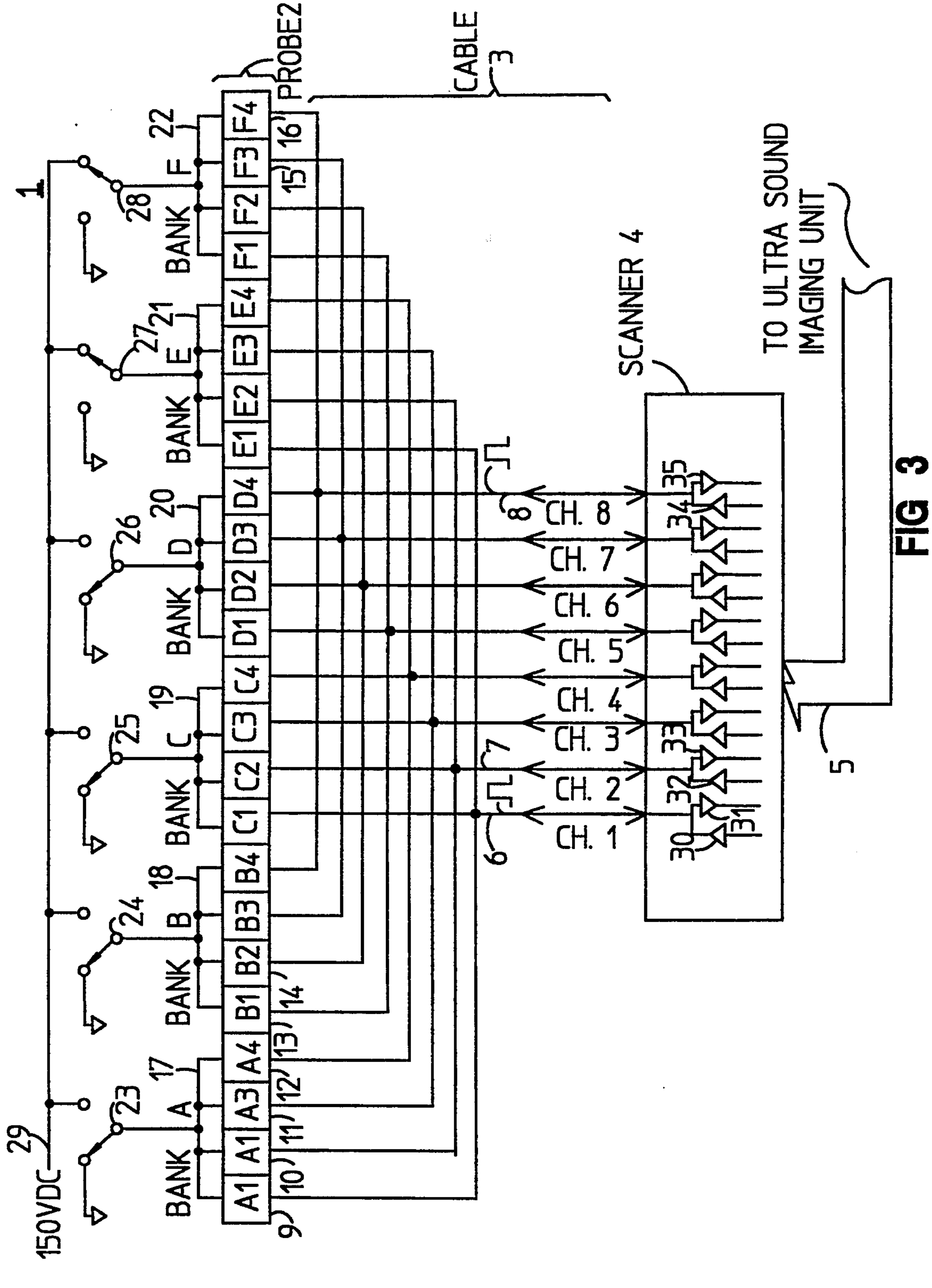
FIG. 3 is the same block diagram as in FIG. 1, but showing a bank selection that positions the aperture at an extreme location on an opposite side of the probe.

The operative principle of how the incorporation of electrostrictive material can reduce the complexity of a scanner for a an ultrasound probe will be illustrated with the aid of the simplified example depicted in FIGS. 1–3. In these figures a particular structure is shown in different phases of its operation, with features that are the same from figure to figure being denoted by reference characters that are likewise the same from figure to figure.

Refer now to FIG. 1, wherein is shown an ultrasound probe arrangement 1 whose probe 2 has twenty-four electrostrictive piezoelectric transducer elements arranged as six banks each having four electrostrictive transducer elements that are interconnected with electrostrictive transducer elements of other banks in a manner described below. The six banks are denoted A through F, and the transducer elements within each bank (e.g., 9–16) are denoted by bank name followed by a digit between one and four, inclusive. The probe 2 is connected by a cable 3 to a scanner 4, which is in turn connected via signal path(s) 5 to an ultrasound imaging unit (not shown).

In the present example the scanner 4 supports eight channels (denoted ch. 1 through ch. 8), or twice the number of transducers in a group. Each channel includes transmit and receive circuitry, which may include, for example, drive amplifiers or switches 30, 32 and 34 for ch's 1, 2 and 8, respectively, and respective receive amplifiers 31, 33 and 35 for those same channels.

Each channel is connected by an associated conductor to transducers in the probe 2. In the example, conductor 6 represents channel 1, conductor 7 represents channel 2, and conductor 8 represents channel 8. Each channel is coupled to a driven side of every eighth transducer element in the probe 2. Thus, ch. 1 is coupled to transducer elements A1, C1 and El, while ch.2 is coupled to transducer elements A2, C2 and E2. In like fashion, ch. 8 is coupled to transducer elements B4, D4 and F4. As will be seen, however, by virtue of the electrostrictive nature of the transducer elements, at any given time only one transducer element per channel is active.

To appreciate this, note that the other sides of the transducer elements are connected together in common, according to the bank they are in. Call these the common, or bias sides, of the electrostrictive transducer elements. Bank A has a common connection 17, bank B has common connection 18, and so on, up to bank F, which has common connection 22. For the present example under consideration, only two adjacent banks of electrostrictive transducer elements will be biased on at any one time; the others will all be biased off. It is this biasing that reduces the number of active transducer elements to one per channel. To bring this about each bank has associated therewith a single pole double throw switching element. Switch 23 is associated with bank A, switch 24 with bank B, and so on, up to switch 28 for bank F. Each switching element switches the common connection for its associated group between a voltage that biases electrostrictive transducers in that group off (e.g., ground) or on, say, 150 volts DC. The DC bias voltage exhibits a good AC ground, however, so as to continue to provide an adequate return path for the drive pulses that excite the transducer elements. Likewise, the circuitry in the scanner provides an adequate return path, or reference voltage at a suitable impedance, for the bias voltage.

The arrangement of FIG. 1 supports moving aperture phased array operation with up to five transducer elements. Phased array operation involves the excitation of a number of adjacent transducer elements in timed relationship, such that the emitted ultrasound spatially reinforces and cancels portions of itself to combine into a beam that is steered in a desired direction and focussed at a selected spot. The receive operation is similarly steered and focussed by suitably delaying the reflected signals before they are summed into a combined signal. The size of the aperture is the number of transducers elements involved in the steering and focussing. For the particular arrangement of FIG. 1, where the scanner covers two banks, the rule is that the aperture can be as large as one plus the number of transducer elements in a bank. As will be seen, the general rule for the type of arrangement shown in FIG. 1 is that the aperture can be as large as one plus the difference between the number of channels in the scanner and the number of transducer elements in a bank.

To continue, note that in FIG. 1 switches 23 and 24 are set to connect banks A and B to a bias voltage of 150 VDC. This polarizes banks A and B, which is to say, biases them on. The remaining switches 25–28 for banks C through F are set to connect those banks to a bias voltage of zero (ground). This turns those banks off. Now channels 1–5 are fired (excited by the application of a high voltage pulse to their electrostrictive transducer elements) in a known appropriate timed sequence for the desired ultrasonic beam (or "line" of ultrasound), which excites electrostrictive transducer elements A1, A2, A3, A4 and B1 (most probably to "fire" a line "centered on" transducer element A3). Transducer elements B2 through B4 are not excited because their channels (6–8) are not fired. Transducer elements C1 through F4 are not excited because they are in banks whose electrostrictive transducer elements are not polarized, or biased on. After an appropriate period of time to allow for the reception of reflected energy, during which time the bank selection switches 23–28 and the channel selections within the scanner 4 remain unchanged, the channel selection within the scanner becomes channels 2 through 6, unless another line centered on A3 is desired in order to measure a doppler shift. Selecting channels 2 through 6 centers the next line on transducer element A4.

The process described above is repeated with ch. 2 through ch. 6, after which it is repeated again with ch. 3 through ch. 7 (to fire a line centered on B1 ), and still then again with ch. 4 through ch. 8 (for a line centered on B2). After that, however, Bank switch 23 is set to connect bank A to ground and bank switch 25 is set to connect bank C to the polarizing voltage 29. Following that change to the bank switches, ch. 5 through ch. 1 are again selected in the scanner. This produces the situation depicted in FIG. 2, and allows the firing of a line centered on B3.

To fire a line centered on B3 requires that transducer elements B1 and C1 be excited, then B2 and B4, followed by B3. This requires the use of ch. 5 and ch. 1, then ch. 6 and ch. 8, followed finally by ch. 7. As before, because of the settings of the bank switches 23–28, only banks B and C exhibit piezoelectric properties.

This general scheme of things continues, with each successive transducer element (save for F3 and F4) being the center of a line of ultrasound fired from the probe 2. The entire scheme for the preceding example can be represented in tabular form as follows:

| CENTER ELEMENT | CHANNELS |
|---|---|
| A3 | 1–5 |
| A4 | 2–6 |
| B1 | 3–7 |
| B2 | 4–8 |
| B3 | 5–8, 1 |
| B4 | 6–8, 1–2 |
| C1 | 7–8, 1–3 |
| C2 | 8, 1–4 |
| C3 | 1–5 |
| C4 | 2–6 |
| D1 | 3–7 |
| D2 | 4–8 |
| D3 | 5–8, 1 |
| D4 | 6–8, 1–2 |
| E1 | 7–8, 1–3 |
| E2 | 8, 1–4 |
| E3 | 1–5 |
| E4 | 2–6 |
| F1 | 3–7 |
| F2 | 4–8 |

At this point it is useful to discuss the relationships between the number of transducer elements in the probe, the aperture, the bank size and the number of channels in the scanner. The most obvious relationship is, as in the example of FIGS. 1–3, that the number of channels in use must be equal to at least twice the number of transducer elements served by a bank (i.e., must be at least twice the bank size). This is needed to allow the retirement of bank K in favor of bank K+2, and then construing bank K+1 as bank K, and K+2 as K+1. The use of three, four, or even, say, eight banks to correspond to the scanner is perfectly possible. In general, the more banks that correspond to the scanner, the better, as it allows the aperture to be larger. This can be seen by noting that a space of one bank size is used to allow stepping by individual transducers for a distance of one bank. The maximum size of the aperture can thus be that of the remaining other banks within the size of the scanner, plus one transducer; the aperture might be smaller. The number of conductors interconnecting the transducer elements of the various banks is one less than the size of the aperture. The number of banks is simply the number needed to provide the necessary number of transducer elements in the probe. In general, the number of banks may be increased without effect to the other parameters.

An example of an actual probe would be an abdominal probe having 288 transducer elements grouped into thirty-six banks each of eight transducer elements. It could be used with a scanner of, say, 128 channels. Since eight divides 128 sixteen times, the maximum aperture would then be eight times fifteen plus one, or 121.

It will be further appreciated that the bank switches used to select which banks of electrostrictive transducer elements are in use may be located in the probe 2 or in the scanner 4. If they are located in the probe then a collection of bank control signals would travel in cable 3 from the scanner 4 to the probe 2. If the bank control switches are located in the scanner 4 then the various actual bank bias voltages themselves would travel in cable 3.

Figure 4:
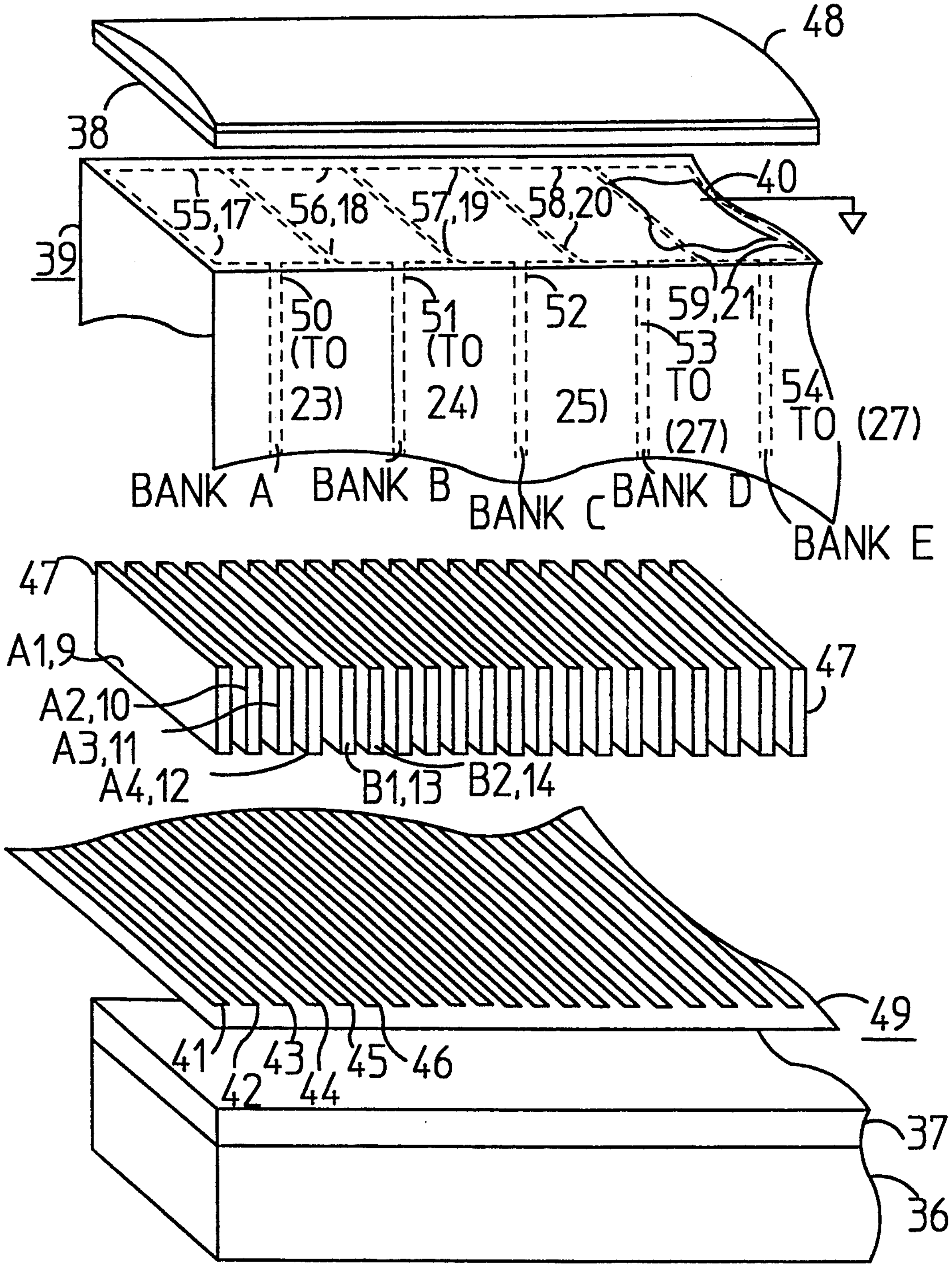
FIG. 4 is a simplified exploded view of one way of fabricating portions of an ultrasound probe having banks of interconnected electrostrictive transducer elements.

FIG. 4 is a simplified exploded view of one manner of fabrication for an ultrasound probe with banks of interleaved electrostrictive transducer elements in general, and of such a probe 1 as in shown in FIG. 1 in particular. The figure shows a transducer element array 47, above which is a section of flexible printed circuit assembly 39 that wraps over the top of the transducer element array 47, above which in turn is an acoustic lens assembly 48. Located below the transducer element array 47 is a flexible printed circuit assembly 49, beneath which in turn are an acoustic matching layer 37 (which is optional) and a foundation 36. It will be understood that in an actual assembled probe those several items would be firmly adhered to one another, and would not appear exploded apart, as is shown in the figure.

The foundation 36 is of a known backing material that may be epoxy loaded with a composite of tungsten, vinyl and phenolic. The function of the foundation 36 is both to support the elements above it and to absorb without reflection the acoustic energy that is (unavoidably) launched in a direction opposite to the lens 48. Just above the (optional) layer 37 of acoustic impedance matching material is an array of closely spaced and parallel conductive traces 41–46 on the upper side of the flexible printed circuit assembly 49. These traces are aligned with the array of transducer elements 47, and make electrical contact therewith on their undersides; the connection so formed is the driven end of the transducer elements. Traces 41, 42, 43 and 44 correspond to the conductors for channel 1, channel 2, channel 3 and channel 4, respectively. Conductor 41, for example, presses against and is conductively adhered to, the driven end of the electrostrictive transducer element at the location indicated by A1, 9. The various transducer elements correspond, as shown, to the elements within the various banks: A1/9, A2/10, A3/11, A4/12, B1/13 and B2/14.

Shown exploded above the array 47 of transducer elements is a U-shaped flexible printed circuit assembly 39, which has traces on both the inside of the U (which come into contact with ends of the transducer elements) and the outside. What is on the outside is a an undifferentiated layer of conductive foil 40 that is connected to ground. Its purpose is to act as a safety shield between the voltages on the inside of the probe and anything on the outside, so that under no reasonably conceivable circumstances can someone be shocked by a failure of one or more parts of the probe. Since the outer shield of conductive foil 40 is simply a uniform layer matching the extent of the assembly 39, it would not be easily depicted in full, and so has been pictorially represented by just a portion of its surface.

On the inside of the flexible printed circuit assembly 39 are various traces. Shown as dotted lines, since they are hidden on an inside surface of flexible printed circuit assembly 39, are traces and pads that are the bias terminals for the various banks. For example, pad 55 corresponds to the connection 17 that interconnects transducer elements A1, A2, A3 and A4, and trace 50 corresponds to the conductor from bank switch 23. Traces 51 through 54 are likewise electrically connected to switches 24 through 27, respectively.

Finally, an acoustic impedance matching layer 38 and acoustic lens 48 are adhered to the top surface of the flexible printed circuit assembly 39. The acoustic impedance matching layer 38 may be one or more layers of materials having suitable acoustic impedance(s), and the material(s) may be used in slab form, as shown, or may be diced or serrated into individual pieces that correspond to and align with the various transducer elements.

We claim:

1. An ultrasound probe comprising:

a first bank of n-many adjacent transducer elements of an electrostrictive material, each of the transducer elements of the first bank having first and second electrical terminals;

a first common electrical connection to which the first terminal of each of the transducer elements of the first bank is electrically connected;

a first voltage source having a voltage adequate for polarizing the electrostrictive material;

a second voltage source having a voltage adequate for depolarizing the electrostrictive material;

a first switching mechanism of single pole double throw configuration and having its pole electrically connected to the first common electrical connection, a first throw that connects the pole to the first voltage source and a second throw that connects the pole to the second voltage source;

a second bank of n-many adjacent transducer elements of electrostrictive material, each of the transducer elements of the second bank having first and second electrical terminals;

a second common electrical connection to which the first terminal of each of the transducer elements of the second bank is electrically connected;

a second switching mechanism of single pole double throw configuration and having its pole electrically connected to the second common electrical connection, a first throw that connects the pole to the first voltage source and a second throw that connects the pole to the second voltage source; and the first electrical terminals of the transducer elements of the first bank being electrically isolated from the first electrical terminals of the transducer elements of the second bank.

2. An ultrasound probe as in claim 1 and further comprising:

a third bank of n-many adjacent transducer elements of electrostrictive material, each of the transducer elements of the third bank having first and second electrical terminals;

a third common electrical connection to which the first terminal of each of the transducer elements of the third bank is electrically connected;

a third switching mechanism of single pole double throw configuration and having its pole electrically connected to the third common electrical connection, a first throw that connects the pole to the first voltage source and a second throw that connects the pole to the second voltage source;

a fourth bank of n-many adjacent transducer elements of electrostrictive material, each of the transducer elements of the fourth bank having first and second electrical terminals;

a fourth common electrical connection to which the first terminal of each of the transducer elements of the fourth bank is electrically connected;

a fourth switching mechanism of single pole double throw configuration and having its pole electrically connected to the fourth common electrical connection, a first throw that connects the pole to the first voltage source and a second throw that connects the pole to the second voltage source; and the respective first electrical terminals of the first and third banks of transducer elements being electrically connected together as n-many respective pairs and the respective first electrical terminals of the second and fourth banks of transducer elements being electrically connected together as n-many respective pairs.

* * * * *